(12) United States Patent
Gordon

(10) Patent No.: US 9,551,215 B2
(45) Date of Patent: Jan. 24, 2017

(54) APPARATUS AND SYSTEM FOR PASSIVELY SAMPLING PRODUCTION FLUID FROM A WELL

(75) Inventor: Alexandre Gordon, Scotland (GB)

(73) Assignee: OneSubsea IP UK Limited, London (GB)

( * ) Notice: Subject to any disclaimer, the term of this patent is extended or adjusted under 35 U.S.C. 154(b) by 367 days.

(21) Appl. No.: 13/584,500

(22) Filed: Aug. 13, 2012

(65) Prior Publication Data

US 2014/0041446 A1   Feb. 13, 2014

(51) Int. Cl.
*E21B 49/08* (2006.01)
*G01N 1/20* (2006.01)

(52) U.S. Cl.
CPC .......... *E21B 49/086* (2013.01); *G01N 1/2042* (2013.01)

(58) Field of Classification Search
CPC ...... E21B 49/08; E21B 49/081; E21B 49/088; E21B 49/086
USPC ........................ 73/152.23, 863.21, 863.71, 73/152.19–152.28
See application file for complete search history.

(56) References Cited

U.S. PATENT DOCUMENTS

| | | | |
|---|---|---|---|
| 7,311,001 B2 * | 12/2007 | Liu et al. | 73/215 |
| 2001/0005986 A1 * | 7/2001 | Matsubara et al. | 55/459.1 |
| 2007/0084340 A1 * | 4/2007 | Dou et al. | 95/8 |
| 2009/0139345 A1 * | 6/2009 | Xie | 73/861.04 |
| 2010/0059221 A1 * | 3/2010 | Vannuffelen et al. | 166/264 |
| 2011/0073306 A1 | 3/2011 | Morrison | |
| 2011/0155385 A1 * | 6/2011 | Haheim | 166/357 |
| 2013/0025874 A1 * | 1/2013 | Saunders et al. | 166/357 |

FOREIGN PATENT DOCUMENTS

| | | |
|---|---|---|
| CN | 2204653 Y | 6/1995 |
| WO | 9934269 A1 | 7/1999 |

OTHER PUBLICATIONS

International Search Report and Written Opinion dated Oct. 18, 2013 for PCT Application No. PCT/US2013/053226 filed Aug. 1, 2013.

* cited by examiner

*Primary Examiner* — Peter Macchiarolo
*Assistant Examiner* — Anthony W Megna Fuentes
(74) *Attorney, Agent, or Firm* — Chamberlain Hrdlicka

(57) ABSTRACT

An apparatus and system for passively sampling production fluid from a well is presented. The passive sampling device is used to split two-phase flow and provide a driving pressure differential for a sampling system. Flow through sampling systems require a low pressure differential to be utilized to take a liquid sample, so that the sample retained remains isobaric. When performed in two-phase flow, the pressure differential needs to be relatively high, potentially yielding a non-isobaric sample. By separating out the liquid content of the flow, a low driving pressure is allowed to be used. Thus, this keeps the sample isobaric at a wide range of production flow rates.

20 Claims, 4 Drawing Sheets

APPARATUS AND SYSTEM FOR PASSIVELY SAMPLING PRODUCTION FLUID FROM A WELL

BACKGROUND

It is useful to know certain characteristics of a borehole for drilling operations. During the lifespan of an oil reservoir, samples of production fluid from the reservoir can be collected and analyzed. In order to effectively sample the production fluid from a subsea well, sampling systems are often located subsea, in close proximity to the wellhead. Wellhead sampling presents a challenge due to the potential for dispersed and mist flow from the wellhead containing both liquid and gas phases (multiphase flow). In order to properly sample multiphase flows the liquid phase must be separated from the gas phase. Multiphase flows exhibiting a dispersed or mist flow regime can be difficult to separate into component liquid and gas phase flows, in turn making the collection of liquid-only samples more difficult.

Conventional sample systems use a flow device, such as a venturi or an orifice plate, to generate a pressure differential that is proportional to the production flow. However, if the production flow rate is too low, the pressure differential generated by the flow device may be insufficient to retain a sample that contains both liquid and gas. Further, for a 2-phase flow (gas-liquid), a high pressure differential is needed to retain a liquid sample. This is due to a high level of turbulence/velocity being required to keep the liquid in a gas suspension.

BRIEF DESCRIPTION OF THE DRAWINGS

A better understanding of the various disclosed system and method embodiments can be obtained when the following detailed description is considered in conjunction with the drawings, in which.

DETAILED DESCRIPTION

Figure 1A:
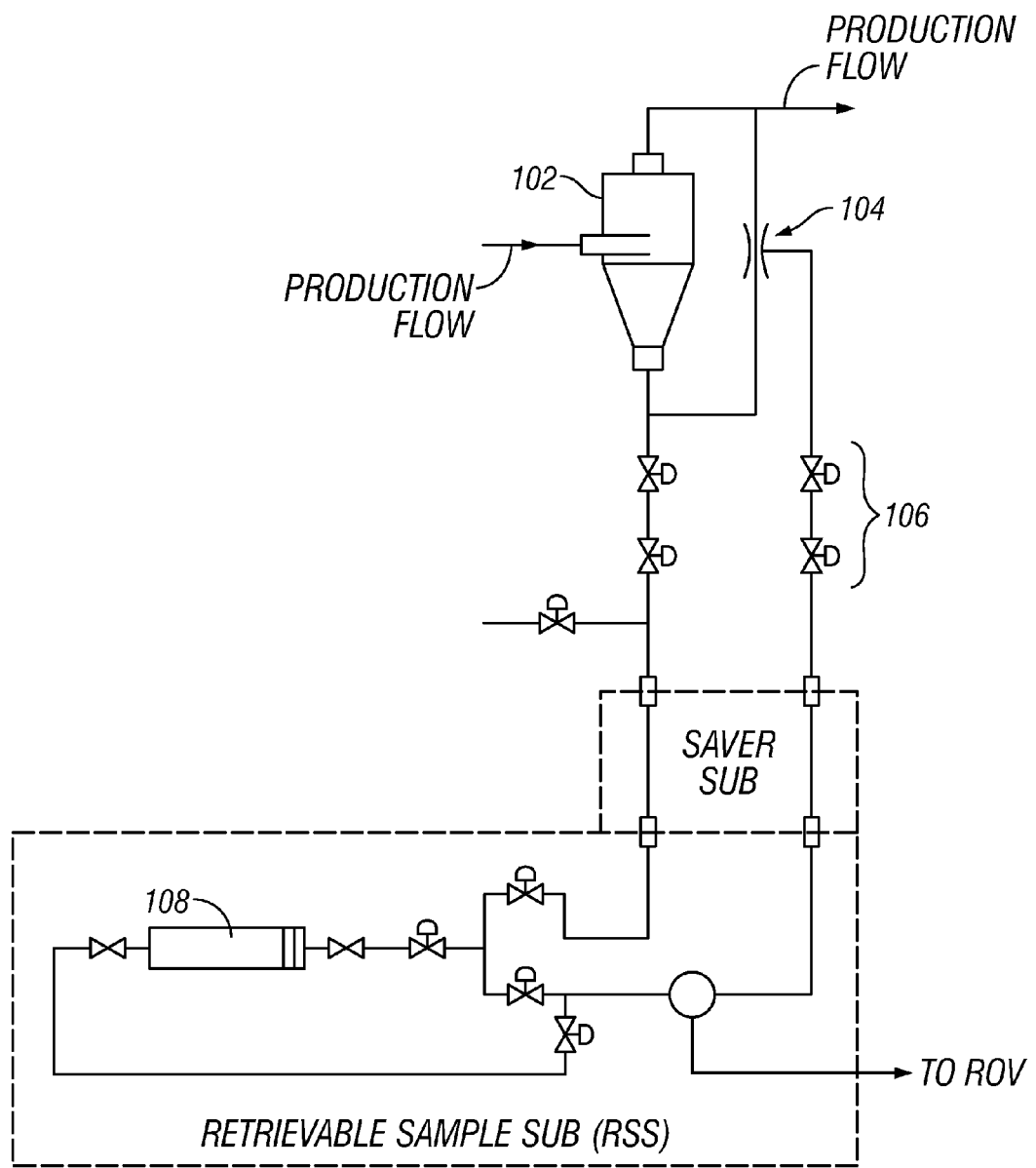
FIGS. 1A-1C are illustrative diagrams of a vortex separator passively-driven system.

The following discussion is directed to various embodiments of the invention. The drawing figures are not necessarily to scale. Certain features of the embodiments may be shown exaggerated in scale or in somewhat schematic form and some details of conventional elements may not be shown in the interest of clarity and conciseness. Although one or more of these embodiments may be preferred, the embodiments disclosed should not be interpreted, or otherwise used, as limiting the scope of the disclosure, including the claims. It is to be fully recognized that the different teachings of the embodiments discussed below may be employed separately or in any suitable combination to produce desired results. In addition, one skilled in the art will understand that the following description has broad application, and the discussion of any embodiment is meant only to be exemplary of that embodiment, and not intended to intimate that the scope of the disclosure, including the claims, is limited to that embodiment.

Certain terms are used throughout the following description and claims to refer to particular features or components. As one skilled in the art will appreciate, different persons may refer to the same feature or component by different names. This document does not intend to distinguish between components or features that differ in name but not function.

In the following discussion and in the claims, the terms "including" and "comprising" are used in an open-ended fashion, and thus should be interpreted to mean "including, but not limited to . . . ." Also, the terms "couple," "connect," "engage," and "attach" are intended to mean either an indirect or direct connection. Thus, if a first device couples to a second device, that connection may be through a direct connection, or through an indirect connection via other devices, components, and connections. The term "fluid" may refer to a liquid or gas and is not solely related to any particular type of fluid such as hydrocarbons. The term "pipe," or the like refers to any fluid transmission means. In addition, as used herein, the terms "axial" and "axially" generally mean along or parallel to a central axis (e.g., central axis of a body or a port), while the terms "radial" and "radially" generally mean perpendicular to the central axis. For instance, an axial distance refers to a distance measured along or parallel to the central axis, and a radial distance means a distance measured perpendicular to the central axis.

Accordingly, disclosed herein is an apparatus and system for passively sampling production fluid from a well. The apparatus for such sampling includes a vortex chamber for separating an inputted multiphase fluid flow into at least a gas phase and a liquid phase. This apparatus includes a chamber with an internal volume, an inlet port configured to input the multiphase fluid flow, a gas outlet port, and a liquid outlet port, and a passive low-pressure sampling device in line with the outlet port. Another apparatus embodiment may include a chamber with an internal volume, an inlet port configured to input the multiphase fluid flow, a gas outlet port, and a vortex separator that creates suction and spins recycled liquids to the wall of the chamber.

The system embodiment for taking samples from a well includes a pipe carrying a multiphase fluid flow, a vortex chamber for separating an inputted multiphase fluid flow that includes a passive low-pressure sampling device, a gas flow pipe, and a liquid flow pipe. The passive low-pressure sampling device is coupled to the liquid portion of the separator to create a pressure differential across the sampling system. Another system embodiment could include a pipe carrying a multiphase fluid flow, a vortex chamber/bottle for separating an inputted multiphase fluid flow that includes a gas flow pipe and a liquid flow pipe connected to its outlets. For this embodiment, a vortex center creates suction and spins recycled liquids to the wall. Secondary separation occurs as the spinning gas converges at the center of the separator.

Another system embodiment can further include a receiving structure positionable on a manifold, a saver sub, and a retrievable skid positionable within the receiving structure. The retrievable saver sub is positionable within the receiving structure, and includes chambers for the collection of sample fluids.

Embodiments of the apparatus and system disclosed can be used for effective and reliable separation of the liquid and gas phase components, even under conditions of high flow rates or high gas fractions where a dispersed or mist flow regime for a multiphase flow exists.

Unlike systems that use a powered pump, the apparatus presented in this application includes a passive device that will be used to split a multiphase flow and provide a driving pressure differential for a sampling system. The present invention separates the multi-phase flow and then uses a pressure differential in the liquid line to draw a sample of the well production fluids. As it is a liquid only sample, the pressure differential required is lower than other systems. This design does not require electric or hydraulic power for operation. However, the present invention could be designed to use batteries to power instruments. Further, this system will work well with high and low gas void fractions, and the pressure loss caused by sampling device is low.

FIG. 1A is an illustrative diagram of a system for passively sampling production fluid from a well. The system includes a vortex separator 102, a passive sampling device 104, operational valves 106, and a sample chamber 108. In this embodiment, the passive sampling device 104 includes a venturi device.

In one embodiment, the system includes a receiving structure that houses a saver sub 130 and a retrievable skid or sample sub 140. The receiving structure can be fixably attached to a manifold, a Christmas tree, or a length of pipe from which samples will be taken. The saver sub 130 accesses the production flow via its connection with the receiving structure and then connects to the retrievable skid. The receiving structure 110 allows samples to be taken throughout the lifecycle of the manifold and the saver sub 130 reduces the number of makes and breaks on the couplings between the manifold and the receiving structure—instead, the interface between the retrievable skid and the saver sub is cycled with every sample taken. Among other valves and couplings, the retrievable skid houses sample collection chambers.

In some embodiments, a remotely operated vehicle (ROV) removes the retrievable skid 140 and brings it to the surface, once the samples have been collected, After the bottles are emptied and replaced in the retrievable skid, it is returned subsea, and reinstalled in the sampling system.

Figure 1B:
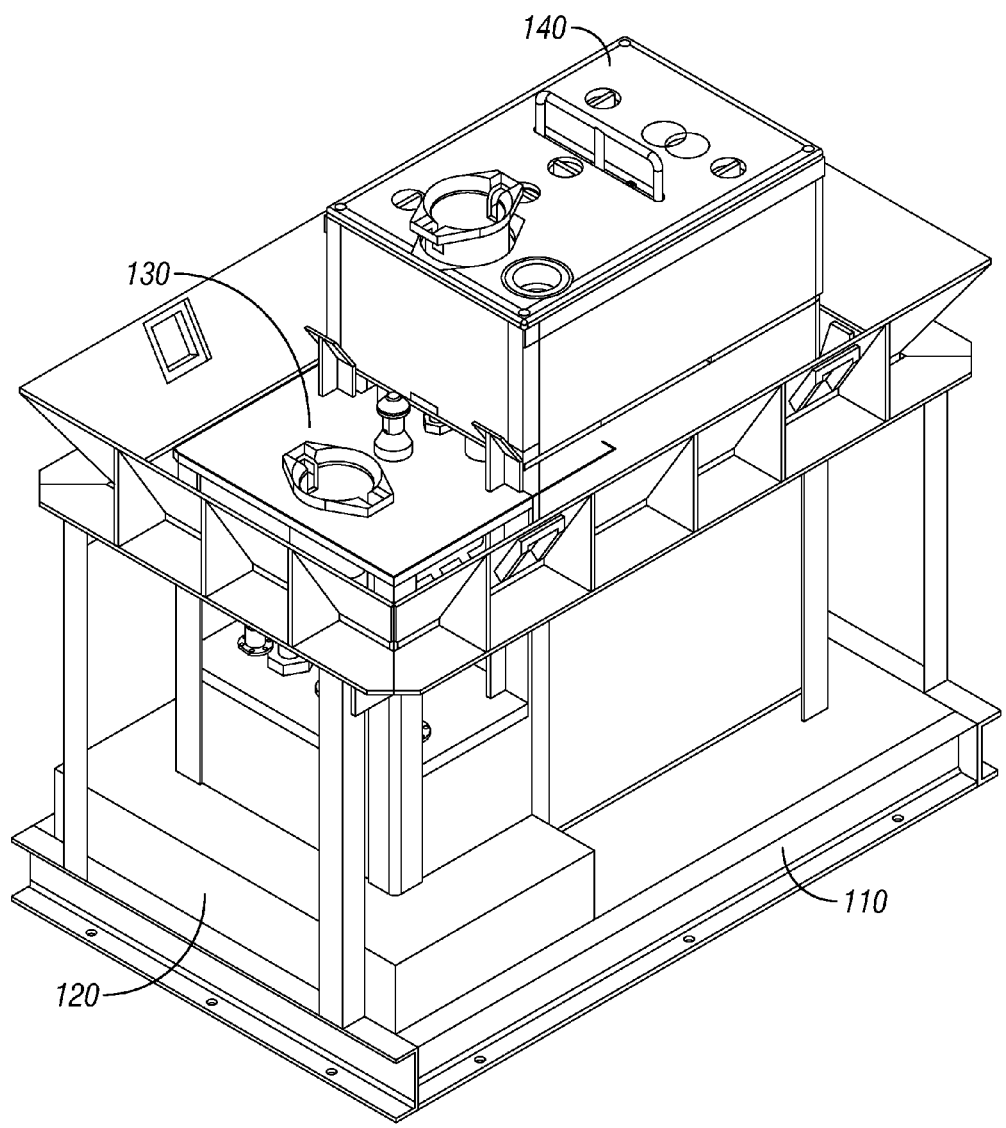
Figure 1C:
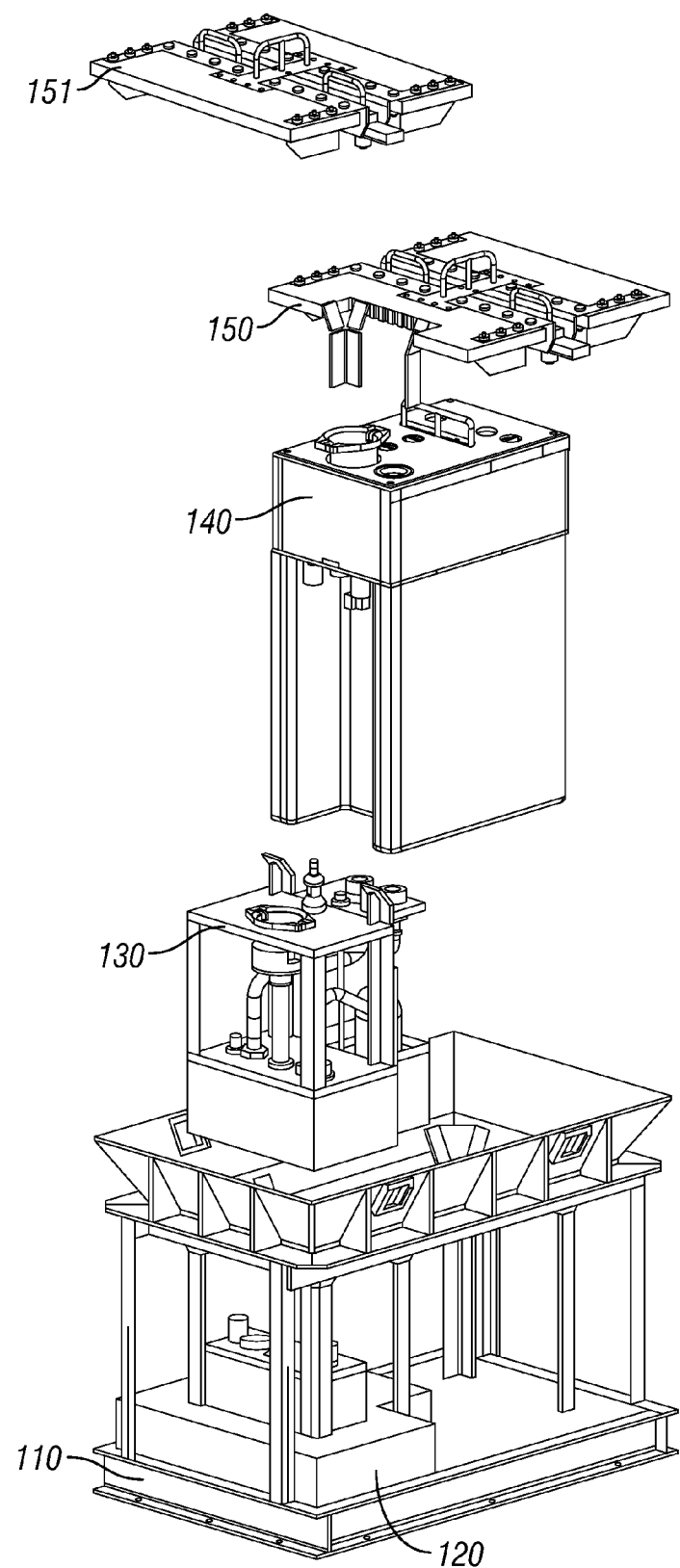

FIGS. 1B and 1C show an embodiment of a sampling assembly for sampling production fluids from an oil or gas well. The well includes a structure, such as a manifold, a Christmas tree, or a length of pipe (not shown, generally referred to as "manifold") and a sampling assembly that includes a receiving structure 110, a saver sub 130, a retrievable skid 140, and protection plates 150, 151. The receiving structure 110 is secured to the manifold, from which production fluid samples will be taken. The receiving structure 110 is connected to the production flow in a manner known to those skilled in the art. The receiving structure 110 is considered non-releasably connected to the manifold, preferably welded into place. Via an ROV, as known to those skilled in the art, the saver sub 130 is guided by and installed on the raised platform 120 of the receiving structure 110. The retrievable skid 140 is installed after the saver sub 130 and is transported and installed via ROV on the receiving structure 110 adjacent to the raised platform 120. In a preferred embodiment, when the saver sub 130 and the retrievable skid 140 are installed in the receiving structure 110, the receiving structure 110 transfers the load from the saver sub 130 and retrievable skid 140 to the manifold.

Figure 2:
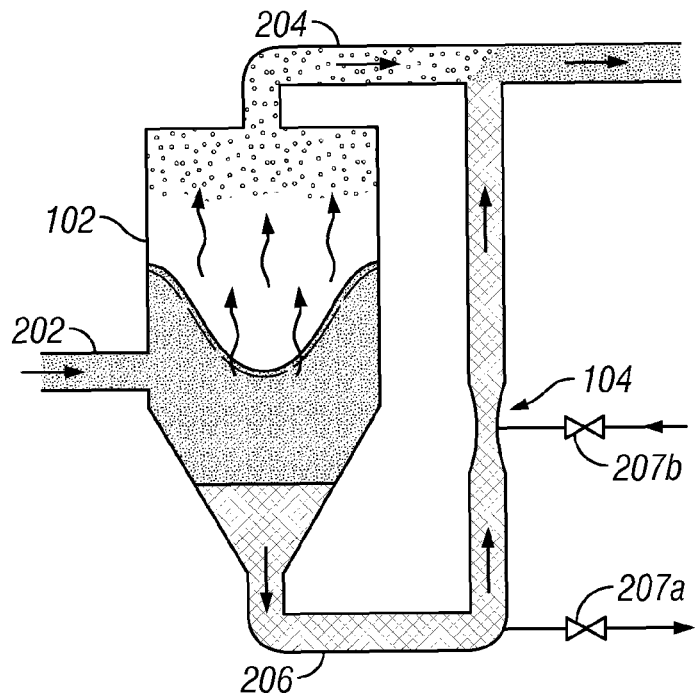
FIG. 2 is an illustrative embodiment of a vortex separator.

As shown in FIG. 2, the passive sampling system includes the vortex separator 102. The system also includes a multiphase inlet 202, a gas phase outlet 204, and a liquid phase outlet 206. Samples are taken and the differential pressure is calculated at the liquid phase outlet 206 near operational valves 207a and 207b. The venturi device 104 is located at near operational valve 207b.

The production flow being sampled enters the vortex separator inlet 202. Here the gas phase and liquid phase are separated, with the gas exiting the gas phase outlet 204 and liquid phase exiting the liquid phase outlet 206. The liquid phase then passes a dead head, which is the inlet of the sampling loop, which includes the sample chamber(s) and associated valves 207a and 207b. Once the liquid has passed the dead head it enters the venturi and the outlet of the sample loop is placed at the point of the venturi, where the flowing pressure is lowest. By using the vortex separator in series with the venturi device (on the liquid portion of the vortex separator), the pressure differential required to take a liquid sample is reduced. This means that a venturi with a larger beta ratio can be used throughout an oil well's life, reducing pressure loss from the production flow and increasing functionality of the sample system.

Figure 3:
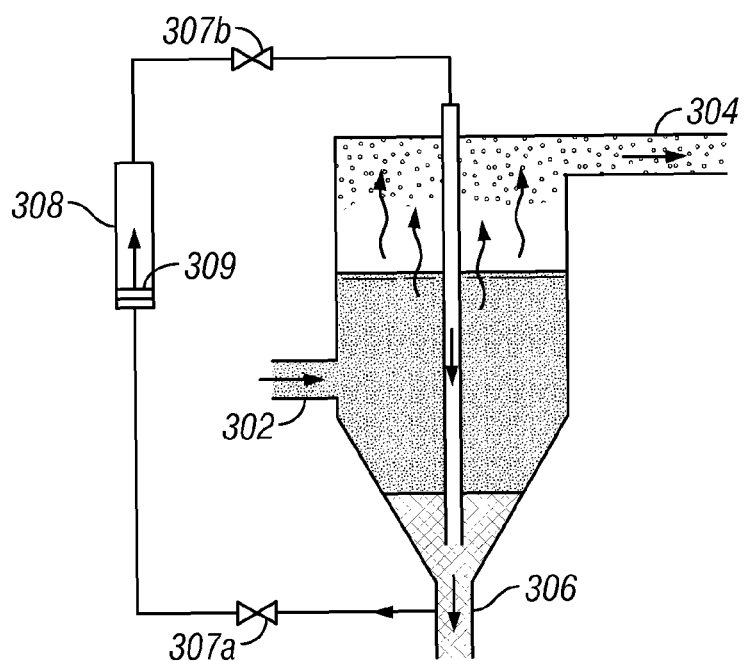
FIG. 3 is an illustrative embodiment of a vortex separator.

Another embodiment of the passive fluid sampling system includes a vortex separator as shown in FIG. 3. The vortex separator includes a multiphase inlet 302, a gas outlet 304, a liquid outlet 306, operational valves 307a and 307b, and a sample chamber 308. A sample is drawn into the sample chamber 308 using the pressure differential across a piston mechanism 309 within the sample chamber 308. In this manner, piston sample chambers can be used by using relatively small difference in pressure to fill them.

Primary separation takes place in the vortex separator as gas enters through a tangential nozzle, creating centrifugal force and forcing the heavier liquid particles to the vessel wall. From there the liquids drain to the stilled chamber in the bottom of the vessel. A low pressure area in the primary separation section created by the spinning gas provides the necessary differential pressure driving force. Some of the advantages of the vortex separator is that it can be constructed to be compact, lightweight, and ideally suited for a separation processes containing moderate amounts of liquid.

Different embodiments for an apparatus and system for separating and sampling an inputted a multiphase fluid flow. The apparatus for such sampling is presented and includes a bottle with an internal volume, an inlet port configured to input the multiphase fluid flow, a gas outlet port, and a liquid outlet port in line with a venturi device. The system embodiment for taking samples includes a pipe carrying a multiphase fluid flow, a vortex chamber for separating an inputted multiphase fluid flow that includes a venturi device, a gas flow pipe and a liquid flow pipe. The venturi device is coupled to the liquid portion of the separator to create a pressure differential across the sampling system. Other embodiments can include alternative variations. These and other variations and modifications will become apparent to those skilled in the art once the above disclosure is fully appreciated. It is intended that the following claims be interpreted to embrace all such variations and modifications.

What is claimed is:

1. An apparatus for passively sampling an inputted multiphase fluid flow, comprising:
    a separation chamber with an internal volume configured to separate the phases of the multiphase fluid into at least a gas phase and a liquid phase;
    an inlet port in fluid communication with the internal volume of the separation chamber for inputting the multiphase fluid flow;
    a gas outlet port in fluid communication with the internal volume of the separation chamber configured to output the gas phase from the separation chamber;
    a liquid outlet port in fluid communication with the internal volume of the separation chamber configured to output the separated liquid phase from the separation chamber;
    a sample chamber; and a passive sampling device in line with the liquid outlet port configured to create a pressure differential sufficient to direct the separated liquid phase into the sample chamber.

2. The apparatus of claim 1, wherein the separation chamber is configured to separate a two-phase flow.

3. The apparatus of claim 1, wherein the separation chamber is a vortex separator.

4. The apparatus of claim 1, wherein the inlet port is angled approximately perpendicular to the separation chamber's central axis.

5. The apparatus of claim 1, wherein the passive sampling device is a venturi device.

6. The apparatus of claim 1, wherein the passive sampling device is a vortex separator.

7. The apparatus of claim 6, wherein the vortex separator is designed to create a pressure differential by inducing a vortex of the separated gas phase resulting in a low pressure area within the internal volume.

8. The apparatus of claim 1, wherein the passive sampling device creates a pressure differential using fluid flow.

9. A system for passively sampling production fluid from a well, comprising:
   a pipe configured to carry a multiphase fluid flow from the well;
   a passive separation and sampling apparatus, comprising:
      a separation chamber with an internal volume configured to separate the phases of the multiphase fluid into at least a gas phase and a liquid phase;
      an inlet port in fluid communication with the internal volume of the separation chamber and configured to input the multiphase fluid flow;
      a gas outlet port in fluid communication with the internal volume of the separation chamber and configured to output the separated gas phase from the separation chamber;
      a liquid outlet port in fluid communication with the internal volume of the separation chamber and configured to output the separated liquid phase from the separation chamber; and
      a passive sampling device in-line with the liquid outlet port;
   a gas flow pipe coupled to the gas outlet port and configured to receive the separated gas phase flow; and
   a liquid flow pipe coupled to the liquid outlet port and configured to receive the separated liquid phase flow.

10. The system of claim 9, wherein the central axis of the chamber's inlet port is disposed at an angle relative to the container's central axis.

11. The system of claim 9, further comprising a sampling container coupled to the liquid flow pipe and configured to store sample fluids.

12. The system of claim 9, wherein the inlet port is angled approximately perpendicular to the separation chamber's central axis.

13. The system of claim 9, wherein the separation chamber is a vortex separator.

14. The system of claim 9, wherein the passive sampling device is a venturi device.

15. The system of claim 9, wherein the passive sampling device is a vortex separator.

16. The system of claim 15, wherein the vortex separator is designed to create a pressure differential by inducing a vortex of the separated gas phase resulting in a low pressure area within the internal volume.

17. The system of claim 9, wherein the passive sampling device creates a pressure differential using fluid flow.

18. The system of claim 9, further comprising a receiving structure positionable on a manifold and a retrievable skid positionable within the receiving structure.

19. The system of claim 18, further comprising:
   the retrievable skid further including chambers for the collection of sample fluids;
   a bottle attachably connected to the passive sampling device; and
   where the bottle can take single or multiphase fluid flow samples a plurality of times throughout the life of production flow.

20. An apparatus for sampling an inputted multiphase fluid flow, comprising:
   a separation chamber with an internal volume configured to separate the phases of the multiphase fluid into at least a gas phase and a liquid phase;
   an inlet port configured to input the multiphase fluid flow into the separation chamber;
   a gas outlet port configured to output the separated gas phase from the separation chamber;
   a liquid outlet port configured to output the separated liquid phase from the separation chamber; and
   a passive sampling device in line with the liquid outlet port.

* * * * *